United States Patent [19]

Davis

[11] Patent Number: 5,064,281
[45] Date of Patent: Nov. 12, 1991

[54] METHOD AND APPARATUS FOR SIMPLIFYING AND IMPROVING CONSISTENCY OF COLOR GRADING OF GEMSTONES

[76] Inventor: Charles E. Davis, 1412 Watrous Dr., Titusville, Fla. 32780

[21] Appl. No.: 669,603

[22] Filed: Mar. 14, 1991

Related U.S. Application Data

[63] Continuation of Ser. No. 548,292, Jul. 3, 1990, Pat. No. 5,005,971.

[51] Int. Cl.⁵ .............................................. G01N 21/87
[52] U.S. Cl. ....................................... 356/30; 356/421
[58] Field of Search ................ 356/30, 421, 422, 423, 356/424; 434/98, 99, 100

[56] References Cited

U.S. PATENT DOCUMENTS

| | | | |
|---|---|---|---|
| 4,527,895 | 7/1985 | Rubin | 356/30 |
| 4,534,644 | 8/1985 | Beesley | 356/30 |

FOREIGN PATENT DOCUMENTS 61-225623 10/1986 Japan .

*Primary Examiner*—F. L. Evans
*Attorney, Agent, or Firm*—James H. Beusse

[57] ABSTRACT

A color grading scale comprises a plurality of individual cast resin chips, each representative of a single color, with the chips attached one to another to form a continuous array of color chips. In a preferred form, the chips are incorporated into a linear slide which fits within a groove formed in a surface of a frame. The frame is formed of a plastic material having a bright white color for maximum white light reflection. Formed in the frame adjacent to and spaced from the groove is at least one shallow pocket having a depth substantially the same as the groove for receiving a gemstone to be color graded by comparison to the color chips of the slide. Plural pockets of different sizes may be provided to accommodate different size stones.

7 Claims, 1 Drawing Sheet

METHOD AND APPARATUS FOR SIMPLIFYING AND IMPROVING CONSISTENCY OF COLOR GRADING OF GEMSTONES

This is a continuation of application Ser. No. 07/548,292, filed 07/03/90, now U.S. Pat. No. 5,005,971.

The present invention relates to color grading of gemstones and, more particularly, to a method and apparatus for simplifying color grading and improving consistency of grading.

BACKGROUND OF THE INVENTION

The economic value of gemstones, particularly diamonds, is highly dependent upon the color of such stones. Within each type of gemstone category, there is a range of color variation which affects value. For diamonds, color variation typically extends from colorless to yellow. Colorless diamonds command the highest prices and may run into thousands of dollars per carat. Diamonds containing a typical yellow tint may cost only a fraction of that of a colorless diamond although a true canary yellow diamond may be relatively expensive.

The presently accepted method for color grading of precious gemstones, such as diamonds, requires comparison of a stone to be graded with stones in a set of certified standard gemstones which may be actual diamonds or synthetic diamonds of cubic zirconium. This method requires extensive training and observations in a standardized light environment. Color grading then requires seeking of a match between one of the stones in the set and the sample stone being graded. The cost of such standardized sets of gemstones precludes their use in many instances.

A further disadvantage of the prior art method of color grading is the inconsistency which routinely appears between trained appraisers and gemologists. Diamonds are typically graded with three separate grades of what is recognized as colorless, i.e., D, E, and F grades are all colorless but there is a slight degradation in progressing from the highest grade D to the lower grade F. Similarly, a near colorless diamond may be graded as G, H, or I grade. Below near colorless grade are size grades ranging from J to 0 which have varying degrees of yellow tints. If any one of these grades of diamonds are examined without reference to the others, it is virtually impossible to determine the diamond color grade. Even when examined as part of a standard set, differences in lighting may affect the appraiser's ability to accurately grade a diamond.

SUMMARY OF THE INVENTION

It is an object of the present invention to provide a method and apparatus for color grading of gemstones which overcomes the above and other disadvantages of the prior art.

It is another object of the present invention to provide a method and apparatus for color grading of gemstones in a consistent manner.

It is another object of the present invention to provide a method and apparatus for color grading of gemstones which is economical and can be accomplished with little training.

The above and other objects are accomplished in a method and apparatus utilizing a color grading scale comprising a plurality of individual cast resin chips, each representative of a single color, with the chips attached one to another to form a continuous array of color chips. In a preferred form, the chips are incorporated into a linear slide which fits within a groove formed in a surface of a frame. The frame is formed of a plastic material having a bright white color for maximum white light reflection. Formed in the frame adjacent to and spaced from the groove is at least one shallow pocket having a depth substantially the same as the groove for receiving a gemstone to be color graded by comparison to the color chips of the slide. Plural pockets of different sizes may be provided to accommodate different size stones.

The apparatus is employed to color grade stones by holding the array of color chips such that edges of the chips are visible and comparing the gemstone to at least some of the chips to identify an approximate color of the gemstone. The array of color chips are placed in a frame having a preselected white coloration with the gemstone being positioned in the frame adjacent to and spaced from the edges of the array of color chips which array is visible from a top surface thereof. The array and the gemstone are moved relative to one another to selectively position the gemstone adjacent each color chip having a color approximately the same as the gemstone as determined by the step of holding the array with an edge of the visible chips. The color chip which most closely approximates the color of the gemstone is selected and the gemstone is graded in accordance with the color grade corresponding to the selected color chip.

BRIEF DESCRIPTION OF THE DRAWINGS

For a better understanding of the present invention, reference may be had to the following detailed description taken in conjunction with the accompanying drawings in which.

DETAILED DESCRIPTION OF THE INVENTION

Figure 1:
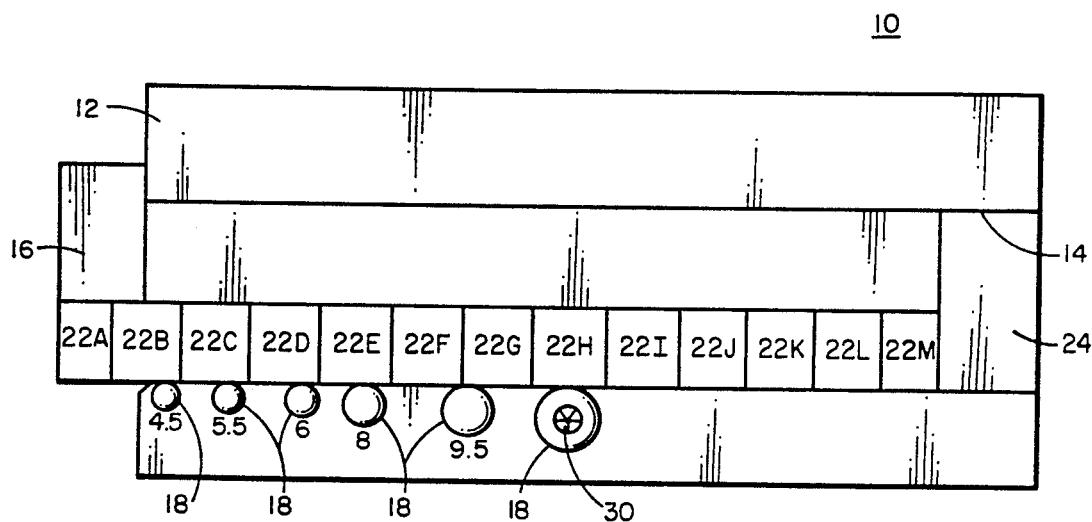
FIG. 1 is a top plan view of one form of gemstone color grading apparatus in accordance with the present invention.
Figure 2:
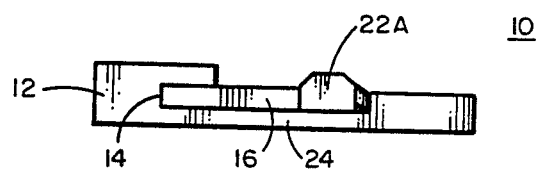
FIG. 2 is an end view of the apparatus of FIG. 1.

FIG. 1 is a top plan view of one form of color grading apparatus 10 in accordance with the present invention. The apparatus 10 includes a frame 12 formed of an acrylic plastic having a high white reflective characteristic. Such high white characteristic is achieved in the plastics industry by addition of Lithium into the plastic resin. The frame 12 includes a groove 14 for receiving a slide 16. The frame also includes a plurality of difference size pockets 18 each located adjacent to one edge of the groove 14. Each pocket 18 includes an aperture opening from the pocket to the groove 14. The pockets 18 are typically of the same depth as the depth of the groove 14. The end view of frame 12 shown in FIG. 2 illustrates a slot 20 at another edge of groove 14 into which slot an edge of slide 16 slidingly fits to allow slide 16 to move with respect to pockets 18 without falling from frame 12.

The slide 16 comprises a plurality of cast plastic tiles or chips 22 arranged in a linear array with each chip bonded to adjacent chips and to an edge support plate 24. The chips 22 each represent a different color varying from colorless at chip 22A to faint yellow at chip 22L. The chips 22 are bonded one to another using a molecular bonding process to eliminate lines at the bonded edges. The bonding process utilizes commercially available plastic bonding agents which include a solvent for softening the plastic of the chips so that they bond at the molecular level. It is important to avoid lines between adjacent chips 22 as will become apparent.

The chips 22 may be formed of a super clear casting resin available from Deep Flex Plastic Molds, Inc. under their model number 065-2402. This resin is a polyester resin which has been found to produce satisfactory results. When the chips 22 are arranged to form the slide 16, they may be protected from scratches by use of a surface hardener such as that available from Environmental Tech, Inc., a liquid hardener for polyester resin.

While there have been prior attempts to develop color grading scales, it is believed that such prior attempts were unsuccessful because of the manner in which they were intended to be used and because the prior attempts did not recognize that each color grade, for example, the J grade, actually has a range of color that can be further separated and that each color chip develops a color which is not only light dependent but dependent upon infused light from adjacent chips. Still further, if a stone to be graded is placed too close to a standard light from the standard, this placement will affect the coloring of the stone. It is also known that the thickness of the chips 22 with respect to a stone being graded will affect color comparison (chip thickness causes shadowing or light reduction). Thus, it is desirable to form the chips 22 to have a thickness of about 0.125 inches. Furthermore, while the chips may be formed with facets on one surface to emulate gemstones, best comparison is attained by viewing a stone against a flat surface and one surface of the chips 22 should remain flat. Obviously, chips 22 must be polished to a high degree using a very fine abrasive to avoid surface deflection.

Accordingly, Applicant has found that the actual color of a standard, i.e., one of chips 22, has to be made different from the color corresponding to a particular color grade. In particular, each color grade can be further divided into three degrees of color variation ranging from "light" to a "darker" coloration. When each of these individual color chips 22 is assembled in an array, light infusion from adjacent chips causes each chip to reflect at a selected midpoint of each color grade, e.g., an F, K, or other value. In order to derive these color values, it is necessary to experiment with various color dyes or tints and it is believed that the proper color grade can only be obtained by empirical testing. Still further, it has been found that oxide dyes are necessary to develop proper color grades. Exemplary dyes are available from Tricon Colors, Inc. using their model numbers 2635 and 3G for oil yellow dyes and 19307 for fluorescent yellow dye. If stones other than diamonds are being considered, color chips may be formed from the same polyester resin material tinted with Tricon Colors, Inc. dyes such as ceres blue, oil red, and tricosal green. An alternative yellow dye available from Atlantic Industries, Inc. is their atlasol yellow 4G and atlasol brilliant yellow LB.

In the use of the present invention to color grade gemstones, testing should preferably be carried out in a room lighted by daylight bulbs of the fluorescent type so that the extreme white color of the frame 12 transfers a maximum amount of light through the color chips 22 into an adjacent one of the pockets 18. A gemstone 30 to be color graded is first cleaned and then placed table down into one of the pockets 18. The slide 16 is removed from the frame 12 and the gemstone 30 observed against the white of the frame 12. The frame 12 may be varied in position by tilting or rotating to thereby vary the light reflected onto the stone. One technique helpful in identifying stone color is to breathe or exhale on the stone to fog it and thereby dull any highlights. The slide 16 is then observed against the white of the frame 12, preferably looking at the edge of the chips 22, and the chips most like the color of the stone are determined. The slide 16 is then placed in the frame 12 and positioned so that the selected chip 22 most like the color of the stone 30 is aligned with the pocket 18 containing the stone. The slide 16 is then moved relative to the pocket while holding the frame at eye level to select the chip 22 having a color most like that of the stone. During the comparison process, it is desirable to maintain a spacing of between about 0.06 and 0.25 inches between the gemstone and the chips 22 to prevent color infusion from the chips to the stone.

The slide 16 may also include specialty variations in gemstones such as a canary yellow diamond having a Z+ color grade as indicated by chip 22M. Since such specialty variations have a wide price differential depending upon whether they are true colors (both appear and fluoresce at the same color) or false colors, it may be desirable to provide chips having such different coloration on the slide 16.

While the invention has been described in what is presently considered to be a preferred embodiment, other modifications and variations will become apparent to those skilled in the art. It is intended therefore that the invention not be limited to the disclosed form but be interpreted within the spirit and scope of the appended claims.

What is claimed is:

1. Apparatus for grading gemstones within a color range comprising:
   a plurality of chips arranged in end-to-end relationship, each of the chips having a hue falling between the hue of each adjacent chip; and
   apparatus for holding said chips in said end-to-end relationship; said apparatus having a uniformly white coloratin for reflecting white light, said chips being held in said apparatus such that said white light is reflected into said chips, said apparatus including a reflecting surface for reflecting said white light toward a gemstone positioned generally adjacent said chips substantially simultaneously with said reflection of white light into said chips whereby coloration of said gemstone may be compared with coloration of said chips.

2. The apparatus of claim 1 wherein each of said chips comprises a clear casting resin mixed with predetermined amounts of a tinting color dye, each chip being tinted differently than its corresponding color grade to accommodate light diffusion effects from adjacent chips.

3. The apparatus of claim 2 wherein each of said chips is formed with a faceted upper portion surrounding a top, substantially flat table surface.

4. The apparatus of claim 1 wherein said chips have a hue ranging from clear to faint yellow.

5. A method for grading gemstones using an array of relatively flat color chips affixed one to another in end-to-end relationship comprising the steps of:

holding the array of color chips such that edges of the chips are visible and comparing a gemstone to be graded to at least some of the chips to identify an approximate color of the gemstone, the array of color chips being held in a support having a preselected white coloration;

positioning the gemstone adjacent to and spaced from the edges of the array of color chips with the array of color chips being visible from a top surface thereof;

moving one of the array and the gemstone relative to one another so as to selectively position the gemstone adjacent to each color chip having a color approximately the same as the gemstone as determined by the stop of holding the array with an edge of the chips visible; and selecting the one of the color chips which most closely approximates the color of the gemstone and grading the gemstone in accordance with the color grade corresponding to the selected one of the color chips.

6. The method of claim 5 wherein the step of selecting includes the step of verifying the selected color grade by viewing the color chips through an edge while the array is positioned in the support and comparing the edge color to the color of the adjacent gemstone.

7. The method of claim 5 wherein the step of selecting includes the further step of exhaling onto the gemstone and array to thereby dull surfaces of the gemstone and array to eliminate bright spots.

* * * * *